United States Patent
Berns et al.

(10) Patent No.: US 11,886,819 B2
(45) Date of Patent: *Jan. 30, 2024

(54) CLASSIFICATION CODE PARSER FOR IDENTIFYING A CLASSIFICATION CODE TO A TEXT

(71) Applicant: IQVIA Inc., Parsippany, NJ (US)

(72) Inventors: Brian Berns, Bethesda, MD (US); Kirk Junker, Hillsboro, VA (US)

(73) Assignee: IQVIA Inc., Parsippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/166,158

(22) Filed: Feb. 8, 2023

(65) Prior Publication Data

US 2023/0186027 A1    Jun. 15, 2023

Related U.S. Application Data

(63) Continuation of application No. 17/105,388, filed on Nov. 25, 2020, now Pat. No. 11,586,821.

(51) Int. Cl.
  *G06F 40/284*    (2020.01)
  *G06F 40/247*    (2020.01)
  (Continued)

(52) U.S. Cl.
  CPC .......... *G06F 40/284* (2020.01); *G06F 40/221* (2020.01); *G06F 40/247* (2020.01)

(58) Field of Classification Search
  CPC ........ G06F 40/12; G06F 40/20; G06F 40/205; G06F 40/247; G06F 40/279;
  (Continued)

(56) References Cited

U.S. PATENT DOCUMENTS 6,915,254 B1    7/2005  Heinze et al.
7,610,192 B1   10/2009  Jamieson
(Continued)

FOREIGN PATENT DOCUMENTS

WO   WO-2016149642 A1 *  9/2016  ............. G06F 15/16
WO   WO-2017089252 A1 *  6/2017  ............. G06F 40/44
WO   WO-2020078954 A1 *  4/2020  ............. G16H 15/00

OTHER PUBLICATIONS

International Preliminary Report on Patentability in International Appln. No. PCT/US2021/060764, dated Jun. 8, 2023, 2 pages.
(Continued)

*Primary Examiner* — Martin Lerner
(74) *Attorney, Agent, or Firm* — Fish & Richardson P.C.

(57) ABSTRACT

A classification code parser and method can include: reading a classification code having a description; reading a required keyword, and a total number of keywords associated with the classification code; reading text of a note; tokenizing the text of the note to create a note token stream, the note token stream having a note token and a position of the note token within the note token stream; creating a keyword map including a total number of matched keywords; determining a match ratio from the total number of the matched keywords and the total number of the keywords; determining a proximity factor based on a shortest span of tokens within the note token stream containing all the matched keywords; and determining a strength of a match between the classification code and the note based on the match ratio being multiplied by the proximity factor.

24 Claims, 6 Drawing Sheets

(51) Int. Cl.
*G16H 15/00* (2018.01)
*G06F 40/221* (2020.01)

(58) Field of Classification Search
CPC ..... G06F 40/284; G06F 40/289; G16H 10/60; G16H 15/00; G16H 50/00
USPC ................ 704/9, 10; 707/729, 723; 705/2, 3
See application file for complete search history.

(56) References Cited

U.S. PATENT DOCUMENTS

| | | | |
|---|---|---|---|
| 8,401,842 B1 * | 3/2013 | Ginzburg | G06F 40/205 |
| | | | 704/10 |
| 9,152,763 B2 | 10/2015 | Carus et al. | |
| 9,734,297 B2 | 8/2017 | Syeda-Mahmood et al. | |
| 9,864,838 B2 | 1/2018 | Goltra | |
| 10,133,727 B2 | 11/2018 | Karres et al. | |
| 10,594,546 B1 * | 3/2020 | Davis | G06F 40/284 |
| 10,629,201 B2 * | 4/2020 | Park | G06F 40/284 |
| 10,650,808 B1 * | 5/2020 | Platt | G06F 40/284 |
| 10,950,329 B2 | 3/2021 | Koll et al. | |
| 11,152,084 B2 | 10/2021 | Kondadadi et al. | |
| 11,157,808 B2 | 10/2021 | Wetta | |
| 11,586,821 B2 * | 2/2023 | Berns | G06F 40/284 |
| 2002/0198739 A1 | 12/2002 | Lau et al. | |
| 2003/0167189 A1 * | 9/2003 | Lutgen | G16H 10/60 |
| | | | 705/3 |
| 2007/0050187 A1 | 3/2007 | Cox | |
| 2008/0133275 A1 | 6/2008 | Haug et al. | |
| 2008/0288292 A1 | 11/2008 | Bi et al. | |
| 2009/0299977 A1 | 12/2009 | Rosales | |
| 2011/0040576 A1 * | 2/2011 | Madan | G16H 15/00 |
| | | | 705/3 |
| 2012/0110016 A1 * | 5/2012 | Phillips | G16H 15/00 |
| | | | 707/780 |
| 2012/0254083 A1 * | 10/2012 | Patrao | G16H 15/00 |
| | | | 706/14 |
| 2012/0290319 A1 | 11/2012 | Saria et al. | |
| 2014/0303981 A1 * | 10/2014 | Skiba | G06F 40/40 |
| | | | 704/270 |
| 2014/0316768 A1 | 10/2014 | Khandekar | |
| 2015/0286619 A1 * | 10/2015 | Chakra | G06F 40/253 |
| | | | 704/9 |
| 2017/0255752 A1 * | 9/2017 | Covit | G16H 70/60 |
| 2017/0323061 A1 | 11/2017 | D'Souza et al. | |
| 2021/0026835 A1 * | 1/2021 | Pai | G06F 40/295 |
| 2021/0334462 A1 * | 10/2021 | Kukreja | G06F 40/295 |
| 2021/0343410 A1 | 11/2021 | Zhang et al. | |
| 2021/0358488 A1 * | 11/2021 | Iyer | G06F 40/30 |
| 2022/0164535 A1 | 5/2022 | Berns et al. | |

OTHER PUBLICATIONS

International Search Report and Written Opinion in International Appln. No. PCT/US2021/060764, dated Feb. 4, 2022, 6 pages.

* cited by examiner

| NOTE TOKEN | POSITION |
|---|---|
| HOW | 0 |
| MUCH | 1 |
| WOOD | 2 |
| WOULD | 3 |
| A | 4 |
| WOODCHUCK | 5 |
| CHUCK | 6 |
| IF | 7 |
| A | 8 |
| WOODCHUCK | 9 |
| COULD | 10 |
| CHUCK | 11 |
| WOOD | 12 |

702 ⟶

704 ⟶  706 ⟵

| KEYWORD | POSITIONS OF KEYWORD IN NOTE |
|---|---|
| CHUCK | 6, 11 |
| MUCH | 1 |
| WOOD | 2, 12 |
| TOOTHPASTE | - |

| KEYWORD | REQUIRED? | KW POSITION |
|---|---|---|
| CHUCK | NO | 6, 11 |
| MUCH | NO | 1 |
| WOOD | YES | 2, 12 |
| TOOTHPASTE | NO | - |

| KEYWORD | PRIMARY? | KW POSITION |
|---|---|---|
| CHUCK | YES | 6, 11 |
| MUCH | NO | 1 |
| WOOD | NO | 2, 12 |
| TOOTHPASTE | NO | - |

418

CLASSIFICATION CODE PARSER FOR IDENTIFYING A CLASSIFICATION CODE TO A TEXT

CROSS REFERENCE TO RELATED APPLICATIONS

This application is a continuation of U.S. patent application Ser. No. 17/105,388, filed Nov. 25, 2020 (now U.S. Pat. No. 11,586,821, issued on Feb. 21, 2023), which is hereby incorporated by reference in its entirety.

TECHNICAL FIELD

This disclosure relates to automated language parsing, more particularly to automated parsing and classification of language utilizing classification codes.

BACKGROUND

Modern companies, organizations, and entire industries have come to rely heavily on digital data management. Data management has become a critically important aspect of successfully operating in many fields including government, engineering, and health.

The medical field, for example, provides a helpful illustration of an industry that relies on accurate and complete records for properly and timely diagnosing, treating, and billing medical patients. Furthermore, the medical industry represents one industry, among many, that employs classification codes as an important piece of data within these records.

Illustratively, the World Health Organization (WHO) is one organization to rely on a family of classification codes. Specifically, the WHO sets forth the International Classification of Diseases (ICD) as a standard diagnostic tool for health and clinical purposes.

These classification codes are found on hospital records and medical charts, together with bills and other medical records and notes. These classification codes are relied upon to ensure that patients get proper treatment and receive appropriate medical bills.

Moreover, the medical field generates massive amounts of written notes and documents, and together with newly digitized historical documents, the manual inclusion of classification codes by medical professionals after the note is generated is impractical and impossible. When medical professionals do include a classification code, the process relies on the professional's ability to look up the code based on their current understanding of the medical facts before them as represented by the patient, lab work, and other diagnostic tools.

Although these classification codes provide an effective tool, a large number of the written notes and documents produced within the medical industry do not include these highly effective classification codes. Doctors and other medical professionals must include classification codes manually or not at all.

As technology advances and medical diagnosis, treatment, and billing rely all the more on automated tools, the need to assign classification codes to medical documents has become an obvious and pressing need, as the documents are difficult to classify by hand and no automated solution exists. Identifying and attaching classification codes to medical documents has therefore been identified as an important area for development of next generation technology impacting timely and accurate diagnosis, treatment, and billing.

Technical solutions are actively being sought that can automatically deduce the correct classification code of text. This technical solution must provide a classification from a written note based on its text alone and must be fast enough to assign classification codes to millions of notes in a single run and over the course of a few hours at most.

As such, there remains a need to automatically identify and associate classification codes with written notes and documents, this need is felt all the more as written notes and documents are digitized together with voice transcripts. Previous technical solutions fall short for many reasons and currently there is no suitable solution for identifying and associating classification codes with written documents.

Any technical solution will require the parsing of text that is not grammatically correct, written in short-hand, or written with many technical terms of art. These texts, for example, are often found in medical notes written by doctors.

Previous solutions fail to provide a parsing solution for text that is not grammatically correct, written in short-hand, or written with many technical terms of art. Previous solutions furthermore fail to set forth a solution for matching the result of a parsed text to a classification code.

One previous solution to parsing text is natural language processing (NLP). The NLP technology, however, operates on data that must have correct grammar with standard vocabulary. This technical limitation prevents doctors notes from being parsed.

Illustratively, a doctor's note could state: "RUL undifferentiated large cell neuroendocrine ca. Size ranges from 1.6×1.3 cm-6.5×5.6×5.6 cm on CT scan. s/p bx RUL +." This note should be classified with an ICD-O-3 code of 8013/3 for Large cell neuroendocrine carcinoma.

However, an NLP would err at the use of acronyms, partial words, terms of art, and symbols. Furthermore, no NLP is known to match a note to a classification code. Not only does NLP fail to provide a solution for matching but is also technically limited in its ability to parse notes having improper grammar and non-standard vocabulary.

Traditional NLPs also produce outputs like syntax trees and named entities rather than the very specific healthcare data elements that can be correlated with a classification ICD-O-3 code, for example. NLPs therefore fail to provide a complete solution for the identification and association of classification codes to text.

Other solutions such as statistical NLP, or machine learning, have also been developed. Statistical NLPs, including machine learning systems, however, require large data sets to train the system, without which the system will fail to provide useful results. Large datasets can be difficult and expensive to construct and, in some cases, enough data simply does not exist to train a statistical system.

Particularly, data used for statistical NLP requires both the data and the outcome associated with the data in order to train the system. The need for large volumes of data combined with the need to have this data adequately and accurately described means that many industries using classification codes will simply not have the data required to train a statistical NLP.

Large datasets are not merely a problem related to logistics or data access but are a result of a technical reliance on guess and check. That is, the statistical NLP technology is trained by guessing and checking a voluminous amount of training documents. Illustratively, a statistical NLP may require over 100 training documents per classification to train. When there are thousands of classifications, the training data requirements become an astronomical technical problem designed into the technology of the statistical NLP itself.

Solutions have been long sought but prior developments have not taught or suggested any complete solutions, and solutions to these problems have long eluded those skilled in the art. Thus there remains a considerable need for technical solutions that can automatically deduce the correct classification code from a note based on its text alone and must be fast enough to assign classification codes to millions of notes in a single run over the course of a few hours at most.

SUMMARY

A classification code parser and methods, providing the automatic identification and association of classification codes with written notes and documents, are disclosed. The classification code parser and methods can include: reading a classification code having a description; reading a required keyword, and a total number of keywords associated with the classification code; reading text of a note; tokenizing the text of the note to create a note token stream, the note token stream having a note token and a position of the note token within the note token stream; creating a keyword map including the required keyword associated with the position based on the required keyword matching the note token and the keyword map including a total number of matched keywords; determining a match ratio from the total number of the matched keywords and the total number of the keywords; determining a proximity factor based on a shortest span of tokens within the note token stream containing all the matched keywords; and determining a strength of a match between the classification code and the note based on the match ratio being multiplied by the proximity factor.

Other contemplated embodiments can include objects, features, aspects, and advantages in addition to or in place of those mentioned above. These objects, features, aspects, and advantages of the embodiments will become more apparent from the following detailed description, along with the accompanying drawings.

BRIEF DESCRIPTION OF THE DRAWINGS

The classification code parser is illustrated in the figures of the accompanying drawings which are meant to be exemplary and not limiting, in which like reference numerals are intended to refer to like components, and in which:

FIG. 7 is a table of a keyword map for the required keyword decision step of FIG. 2.

FIG. 8 is a table of a required keyword test for the required keyword decision step of FIG. 2.

DETAILED DESCRIPTION

Figure 1:
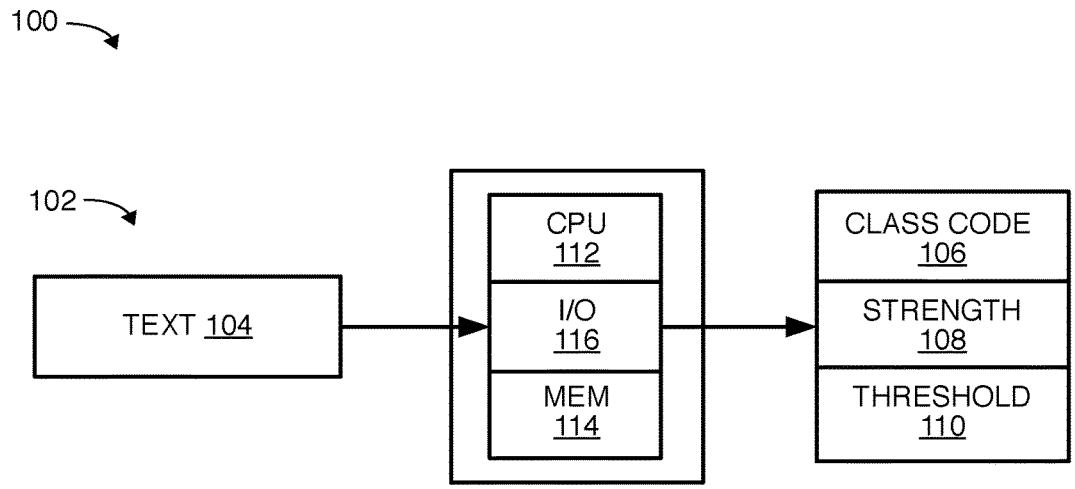
FIG. 1 is a block diagram of the classification code parser.

In the following description, reference is made to the accompanying drawings that form a part hereof, and in which are shown by way of illustration, embodiments in which the classification code parser may be practiced. It is to be understood that other embodiments may be utilized and structure or method changes may be made without departing from the scope of the classification code parser.

When features, aspects, or embodiments of the classification code parser are described in terms of steps of a process, an operation, a control flow, or a flow chart, it is to be understood that the steps can be combined, performed in a different order, deleted, or include additional steps without departing from the classification code parser as described herein.

The classification code parser is described in sufficient detail to enable those skilled in the art to make and use the classification code parser and provide numerous specific details to give a thorough understanding of the classification code parser; however, it will be apparent that the classification code parser may be practiced without these specific details. Furthermore, when specific details, numbers, or equations are described it is to be understood that equivalents of the specific details, numbers, or equations can be used without departing from the classification code parser.

In order to avoid obscuring the classification code parser, some well-known system configurations and descriptions are not disclosed in detail. Likewise, the drawings showing embodiments of the system are semi-diagrammatic and not to scale and, particularly, some of the dimensions are for the clarity of presentation and are shown greatly exaggerated in the drawing FIGS.

The classification code parser disclosed herein is contemplated to be used to parse and classify notes arising in many industries and fields where classification codes are used. For ease of description and technical clarity, one classification code of many used in one particular industry will be used to illustrate the classification code parser.

Particularly, the ICD-O-3 morphology code is a classification code used in the medical industry to classify tumors and is used herein to illustrate the various technical aspects of the classification code parser when reference to a current classification code is useful for descriptive clarity. However, it is to be understood that the classification code parser offers the ability to parse and classify notes using other classification codes found in the medical industry or other industries entirely.

Referring now to FIG. 1, therein is shown a block diagram of the classification code parser 100. The classification code parser 100 can be initialized once and then it can be used to parse as many notes 102 as desired. For expository purposes, the notes 102 are described as digital and having digital text 104.

However, it is contemplated that the classification code parser 100 could operate on equivalents to a digital note also. For example, an equivalent sound recording or a handwritten note could be used as an input as well.

When the input does not include the text 104 in a digital form, the classification code parser 100 can extract the digital text 104 by transcribing the audio recording or through optical text recognition. The classification code parser 100 can output a single classification code 106 with a corresponding strength 108, or no classification code 106 at all.

The user may choose to ignore matches of the classification code 106 that fall below a strength threshold 110. Illustratively, non-pathology notes 102 with a strength 108 of less than 0.1, for example, tend to be false positives, and can usually be ignored.

When the note 102 is not obtained in a text format, the classification code parser 100 can transcribe audio or optically recognize text within a central processing unit 112. The central processing unit 112 can also process and parse the text 104 based on the steps, functions, and processes described herein.

The text 104, the classification code 106, the strength 108, the strength threshold 110 together with intermediate values and calculations can be stored within memory 114. The memory 114 can be volatile, semi-volatile, or non-volatile computer readable medium. The classification code parser 100 can further include input/output elements 116.

The input/output elements 116 can include digital transceivers for transmitting and receiving data from peripherals and within the computer. The input/output elements 116 can also include visual or audio displays and visual, audio, and textual inputs such as cameras, microphones, and keyboards.

Figure 2:
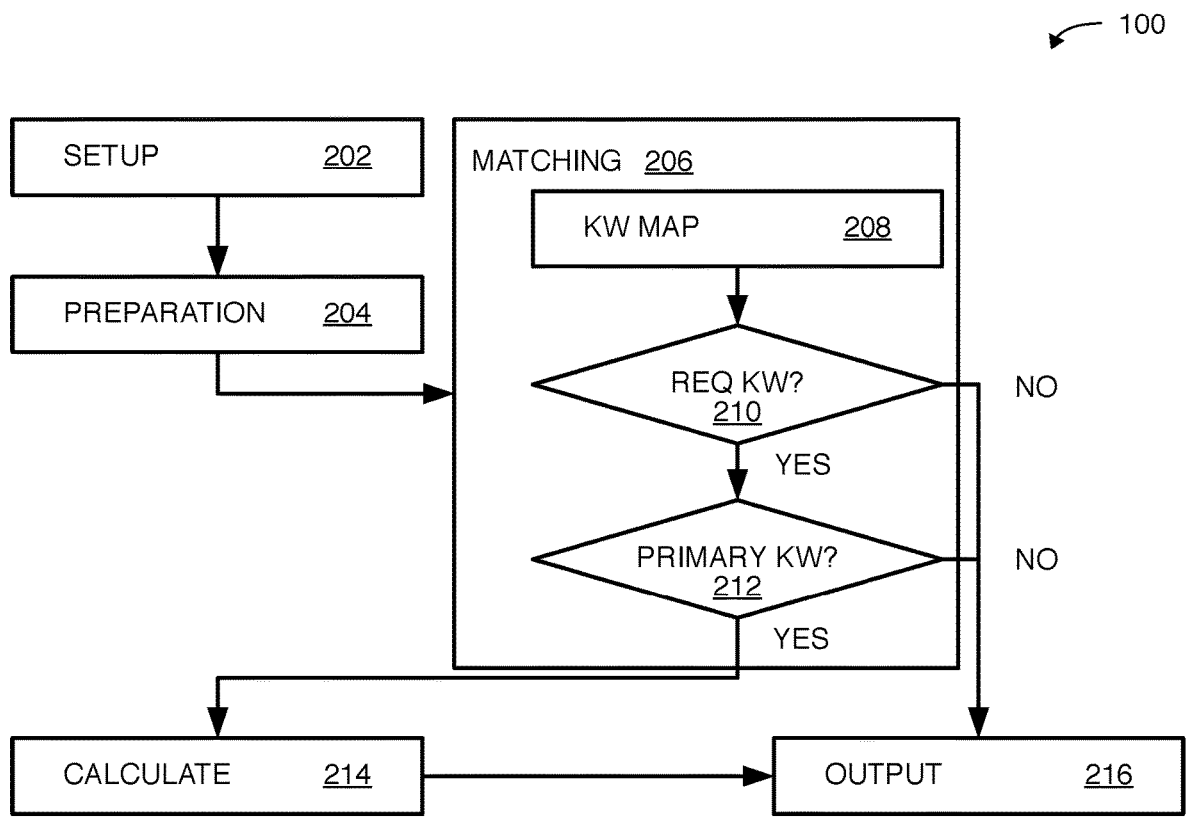
FIG. 2 is a control flow overview of the classification code parser of FIG. 1.

Referring now to FIG. 2, therein is shown a control flow overview of the classification code parser 100 of FIG. 1. The classification code parser 100 can first initiate an initial setup step 202.

The setup step 202 can be an initialization of the classification code parser 100, prior to use. Once the classification code parser 100 has been initialized, it can then be used to parse as many notes 102 of FIG. 1 as desired.

As discussed in greater detail below with regard to FIG. 4, during the setup step 202, the classification code parser 100 can read the classification code 106 of FIG. 1, such as the ICD-O-3 morphologies, from a file. Furthermore, the setup step 202 can include reading a list of synonyms, secondary keywords, and ignored tokens.

Once the setup step 202 is complete, the classification code parser 100 can follow the same sequence of steps for each of the notes 102 beginning with a preparation step 204. The preparation step 204 can read the text 104 of the note 102 and tokenize the text 104 of the note 102, which includes the process of breaking the text 104 of FIG. 1 into individual words ("tokens"). The preparation step 204 can further include the removal of negative content from the note 102, and synonym replacement within the note 102.

The classification code parser 100 can then execute a matching step 206. The matching step 206 can include constructing a keyword map of the text 104 within the note 102 as well as checking the text 104 for required keywords and primary keywords.

The matching step 206 can find keywords that are present in both the note 102 and in the list of classifications. Specifically, the classification code parser 100 can execute a keyword mapping step 208 and a required keyword decision step 210 followed by a primary keyword decision step 212; each of which will be described in greater detail below with regard to FIG. 10.

It is contemplated that the operational order of the required keyword decision step 210 and the primary keyword decision step 212 could be reversed without deviating from this disclosure of the classification code parser 100. The keyword mapping step 208 can be used to create the keyword map 702 of FIG. 7. The required keyword decision step 210 can determine whether the text 104 of the note 102 includes all the required keywords for the classification code 106.

The classification code parser 100 can next execute the primary keyword decision step 212, in which the classification code parser 100 can determine whether the note 102 includes at least one primary keyword. As will be described below with regard to FIG. 4, the required keywords and the primary keywords are determined during the setup step 202.

If the classification code parser 100 returns a positive result from both the required keyword decision step 210 and the primary keyword decision step 212, the classification code parser 100 can execute a calculate step 214. During the calculate step 214, the strength 108 of FIG. 1 of the match between the classification code 106 and the note 102 is determined.

Once the calculate step 214 has determined the strength 108 of the match, the classification code parser 100 can execute an output step 216 and display the classification code 106 and the strength 108. Otherwise, if the required keyword decision step 210 or the primary keyword decision step 212 return a negative result, the output step 216 can be executed and return a result with none of the classification codes 106.

Figure 3:
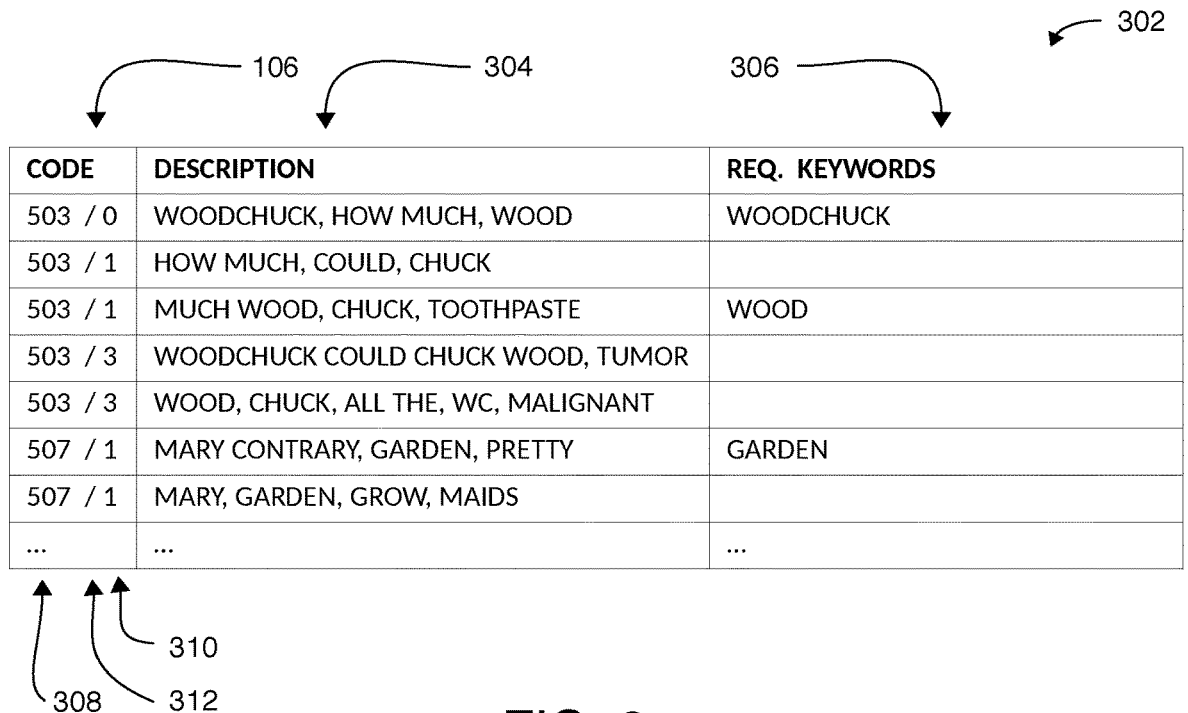
FIG. 3 is a classification code table for use with the classification code parser of FIG. 1.

Referring now to FIG. 3, therein is shown a classification code table 302 for use with the classification code parser 100 of FIG. 1. The classification code table 302 can include the classification codes 106 listed in rows and arranged in a first column.

The classification codes 106 can be listed together with an associated description 304 in a second column and associated required keywords 306 in a third column. It is contemplated that the classification codes 106 are each representative of an ICD-O-3 morphology, which is consists of the classification code 106, such as "8011/3", and the description 304, which is called a "morphology", providing a textual description of the classification code 106, such as "Epithelioma, malignant".

It is contemplated that other classification codes 106 could be used such as ICD-10, and the classification code table 302 for an ICD-10 classification code 106 would include the classification code 106, the description 304, and the required keywords 306. ICD-10; however, would utilize "topography codes" for the description 304 rather than the morphology codes used within the ICD-O-3 code.

A list of the required keywords 306 that are required in order to match the classification code 106, are also shown but are not included in the ICD-O-3 standard. Instead, as described below, the required keywords 306 are included as part of the setup step 202 of FIG. 2. The required keywords 306 can be hand-tuned for each of the descriptions 304 in order to avoid false negatives. The required keywords 306 can be hand-tuned by first identifying false matches and then including additional description tokens as the required keywords 306, which can be required for a match between the note 102 of FIG. 1 and the description 304.

The required keywords 306 are words that must be present within the text 104 of the note 102 of FIG. 1 in order to match one of the classification codes 106 associated with the required keyword 306. As depicted, the required keyword 306 "woodchuck" must be present in the note 102 in order for the classification code 106 "503/0", shown as the first row, to be associated with the note 102.

There might be multiple textual descriptions 304 for each of the classification codes 106, meaning that the same classification code 106 can be listed multiple times in the first column and each time a different description 304 can be provided. Each of these separate listings of the classification code 106 is treated as a separate morphology by the classification code parser 100.

The classification code 106 is shown being comprised of three parts; a type code 308, a behavior code 310, and a separation character 312 therebetween. It is contemplated that the type code 308 can be an alpha-numeric code such as the morphology code from the ICD-O-3 standard or the topography code from the ICD-10 standard.

Illustratively, when the type code 308 is implemented with the ICD-O-3 standard, the type code 308 can be the first four digits of the classification code 106 and would indicate the histology or cell type. Alternatively, when implemented with the ICD-10 standard the type code 308 could indicate the topography, or the site of origin.

It is further contemplated that the classification code 106 may be used with only the type code 308 and without utilizing the behavior code 310 or the separation character 312, which can be the case when implemented with IEEE or government classification codes, for example. The behavior code 310 can be the fifth digit in an ICD-O-3 classification code 106, while the separation character 312 can be a "/" or other equivalent symbols.

Although the classification code 106 is described with regard to the ICD-O-3 standard, it is contemplated that other alpha-numeric characters can be used and defined by convention. The classification code 106 is illustratively depicted having the type code 308 indicating either "503" or "507" while the behavior code 310 is shown as a 0, 1, or 3.

The type code 308 with the value of "503" is shown listed in multiple rows, corresponding to multiple different descriptions 304. The same is shown for the type code 308 with the value of "507".

The behavior code 310 associated with the type code 308 can be different and can be based on the description 304. Illustratively, the behavior code 310 "0" can correspond to benign, "1" can correspond to an uncertainty between benign or malignant, "2" can correspond to carcinoma in situ, and "3" can correspond to malignant. Other behavior codes 310 can be used, but for clarity, are not discussed here.

The classification code table 302 can be stored in and retrieved from the memory 114 of FIG. 1 using the central processing unit 112 of FIG. 1. The classification code 106, the description 304, and the required keyword 306 are to be considered technical parameters for controlling the central processing unit 112 when executing at least the matching step 206 and calculate step 214, both of FIG. 2.

Figure 4:
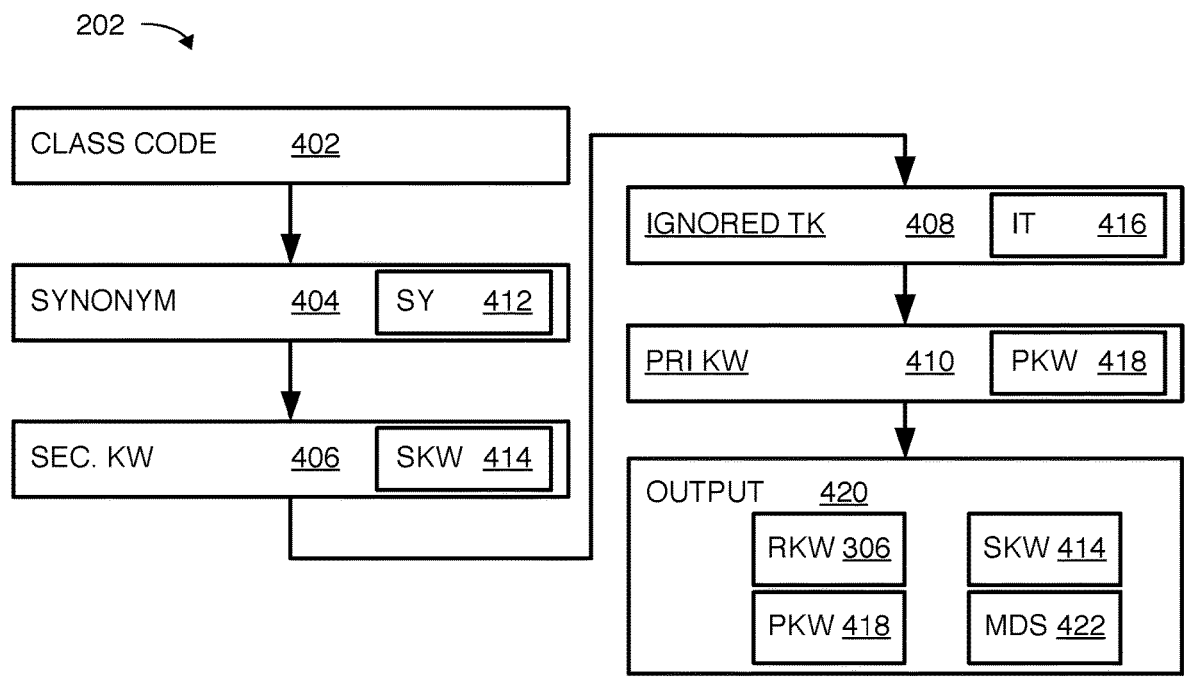
FIG. 4 is a control flow of the setup step of FIG. 2.

Referring now to FIG. 4, therein is shown a control flow of the setup step 202 of FIG. 2. In one instance of the classification code parser 100 of FIG. 1, it must be initialized via the setup step 202 before it can be used; thereafter, it can be used to parse as many of the notes 102 of FIG. 1 as desired.

The setup step 202 can include a read classification code step 402, a read synonym step 404, a read secondary keyword step 406, a read ignored token step 408, and a define primary keyword step 410. During the read classification code step 402, the classification code parser 100 can read the classification code 106 of FIG. 1 with the descriptions 304 of FIG. 3 using the central processing unit 112 of FIG. 1. The classification code 106 with the descriptions 304 can be stored in the memory 114 of FIG. 1.

In one contemplated embodiment, the read classification code step 402 can include reading and storing the classification codes 106, with the descriptions 304, from the ICD-O-3 standard. The descriptions 304 are then tokenized using the central processing unit 112 and stored in the memory 114 as description tokens. The description tokens are to be understood as functional data that serves to control the operation of the central processing unit 112.

Any of the classification codes 106 with the behavior code 310 of FIG. 3 other than "2" or "3", can be filtered out prior to being stored within the memory 114. This is a practical consequence of actual cancer pathology notes 102 using the behavior codes: "2" and "3" almost exclusively. The classification codes 106 associated with the other behavior codes: 0, 1, 6, and 9 are filtered out to avoid false positives.

The classification code parser 100 can execute the read synonym step 404 to obtain description synonyms 412. The description synonyms 412 can match a synonym to one of the description tokens. Illustratively, a description token "SCC" can match with the description synonym "squamous cell carcinoma", and the description token "Hodgkins" can match a description synonym "Hodgkin".

These description synonyms 412 are defined manually and replace all matching description tokens. That is, when one of the descriptions 304 contains one of the description tokens matching one of the description synonyms 412, the description token will be replaced with the description synonym 412 and description 304 will be saved in memory 114 with the description synonym 412 as one of the description tokens.

Once the description tokens are replaced with the description synonyms 412, the classification code parser 100 can execute the read secondary keyword step 406. Secondary keywords 414 can be keywords that can contribute to the strength of a match between the text 104 of FIG. 1 of the note 102 and the description 304, but are not sufficient on their own to establish a match to any description 304.

The secondary keywords 414 are determined manually and are usually generic medical terms that show up in many different contexts. For example, "acute", "cell", and "disease" may all be classified as the secondary keywords 414.

The secondary keywords 414 can be retrieved from the memory 114 by the central processing unit 112. The secondary keywords 414 can be identified for each of the descriptions 304.

The classification code parser 100 can next execute the read ignored token step 408. Ignored tokens 416 can be a list of words that are considered irrelevant by the classification code parser 100, and thus do not contribute to the strength of a match between the text 104 and the description 304.

This is the case, even when the ignored tokens 416 are present in the description 304. The list of the ignored tokens 416 is determined manually and retrieved from memory 114.

Ignored tokens 416 usually consists of short words, such as "all", "and", and "of". The descriptions 304 can be searched and the ignored tokens 416 removed prior to being saved within the memory 114.

The classification code parser 100 can next execute the define primary keyword step 410. The define primary keyword step 410 can read a list of all the description tokens from memory 114 and filter out the secondary keywords 414 and the ignored tokens 416. The description tokens that remain are considered primary keywords 418.

The primary keywords 418 are identified and stored in the memory 114. Thus, the secondary keywords 412 prevent matches between the note 102 and the classification code 106 that consist entirely of the secondary keywords 412 because the primary keyword 414 is any description token that is not explicitly marked as being secondary or an ignored token.

An output 420 or result of the setup step 202 are tokens which are the required keywords 306, the secondary keywords 414, and the primary keywords 418 for each of the descriptions 304. Furthermore, a modified description 422 can be provided for each of the descriptions 304. The modified descriptions 422 can be the original descriptions 304 with the description synonyms 412 replaced and the ignored tokens 416 removed.

Figures 5, 6:
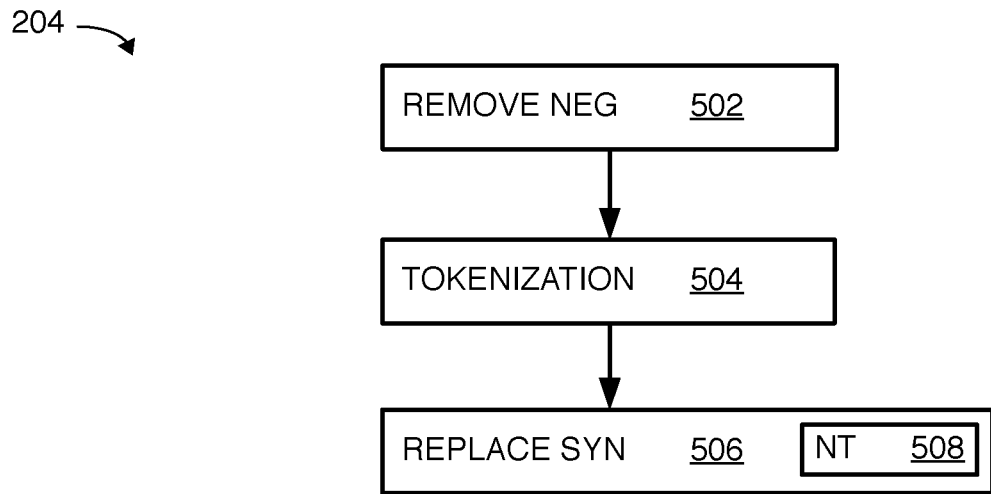
FIG. 5 is a control flow of the preparation step of FIG. 2.
FIG. 6 is a note token position table of the note tokens resulting from the preparation step of FIG. 5.

Referring now to FIG. 5, therein is shown a control flow of the preparation step 204 of FIG. 2. The preparation step 204 can function to extract relevant information from the text 104 of the note 102, both of FIG. 1, once the note 102 has been read by the central processing unit 112 of FIG. 1.

The preparation step 204 can begin with a remove negative content step 502 followed by a tokenization step 504 and a synonym replacement step 506. It is contemplated that in some embodiments the tokenization step 504 could precede the remove negative content step 502. However, if the tokenization step 504 is performed first, the classification code parser 100 of FIG. 1 would need to preserve information about sentence boundaries.

The preparation step 204, including the remove negative content step 502, the tokenization step 504, and the synonym replacement step 506 are implemented utilizing the central processing unit 112. These steps solve the previous technical challenges parsing notes using non-standard terminology and grammar. Tokenizing the note, sensitive to synonyms, negative content, and ignored tokens allows the classification code parser 100 to operate on non-standard notes and ultimately match the classification code 106 of FIG. 1 to the note 102 in reliance on techniques a human user would not employ. Therefore, tokenizing with the central processing unit 112 is a necessary requirement to provide a solution for previous parsing technologies and the classification code parser 100 could not be operated without it.

The remove negative content step 502 can be implemented by the central processing unit 112 to remove negative content from the notes 102 in order to avoid false matches. For example, if the note 102 says "negative for urothelial carcinoma", the note 102 should not match the classification code 106 for carcinoma.

The remove negative content step 502 can proceed by first splitting the note 102 into sentences, at every period or newline character. Negative content is identified as any portion of a sentence that starts with a negative word, such as "no", "negative", or "neg".

The negative content is then trimmed or deleted from the end of each sentence. Once the negative content is removed, the sentences, whether trimmed or not, are joined back together.

In the preferred embodiment, once the remove negative content step 502 is completed, the classification code parser 100 can execute the tokenization step 504. The tokenization step 504 is the process of breaking the text 104 of the note 102 into individual words or note tokens 508. For example, when the text 104 of the note 102 is input as: "Hello, my name is John.", the central processing unit 112 can provide the following the note tokens 508 as a note token stream: "hello", "my", "name", "is", and "john".

The classification code parser 100 can utilize the central processing unit 112 to identify the note tokens 508 using the following process. First, the text 104 is split at whitespace and punctuation. Next the split text is converted to lowercase. The conversion to lowercase requires a first match between the split text and a list of special tokens.

The list of special tokens is read from memory, and all of the split text matching the special tokens are allowed to remain uppercase. For example, "ALL" is a type of leukemia, while "all" is a common English word. When the tokenization step 504 is run, "ALL" would remain capitalized since it matches with an entry found in the list of special tokens. All of the split text that is not found in the list of special tokens is converted to lowercase.

The list of special tokens also identifies tokens that should be joined. If the split text matches any of the special tokens, the split text can be joined. For example, "in" followed by "situ" is unified to a single "in situ" token, while "non" followed by "small" is unified to "non-small".

Thus, the remove negative content step 502 and the tokenization step 504 control the technical functioning of the central processing unit 112 and the memory 114. The classification code parser 100 therefore relies on these technical means to tokenize and extract relevant information from the text 104.

Once the tokenization step 504 has been completed, the classification code parser 100 can execute the synonym replacement step 506. During the synonym replacement step 506, the classification code parser 100 can read the list of description synonyms 412 of FIG. 4. Any of the note tokens 508 that match one of the synonyms in the list of description synonyms 412 can be replaced.

For example, if one of the note tokens 508 is "SCC", this will be replaced with "squamous cell carcinoma" as SCC and squamous cell carcinoma can be identified as synonyms in a list of the description synonyms 412. Continuing with this example, if the stream of note tokens 508 includes: "rll, scc, lesion"; then, the stream of note tokens 508 after the synonym replacement step 506 would be: "rll, squamous, cell, carcinoma, lesion".

Importantly, the synonym replaced is also tokenized and included in the output with the note tokens 508. The note tokens 508 can be stored and retrieved from the memory 114 with the central processing unit 112, and the note tokens 508 are to be understood as functional data that serves to control the operation of the central processing unit 112.

Furthermore, note tokens 508 as described herein provide at least one technical solution to the previous technical problems of NLPs which is solved by parsing text that does not rely on proper grammar or vocabulary. More particularly, the special tokens including the split text and uppercase are but one of the ways non-standard vocabulary and grammar can be parsed with the classification code parser 100.

Referring now to FIG. 6, therein is shown a note token position table 602 of the note tokens 508 resulting from the preparation step 204 of FIG. 5. Illustratively, the note tokens 508 shown can be provided based on the note 102 of FIG. 1 reading: "how much wood would a woodchuck chuck if a woodchuck could chuck wood." The note tokens 508 are provided as a list with a token position 604 of the note token 508 within the stream of the note tokens 508 output from the preparation step 204 rather than the text 104 of FIG. 1.

In this way the position 604 would depend on the replacement of the description synonyms 412 of FIG. 4, as the note tokens 508 were provided as a stream. The position 604 for the note tokens 508 is calculated by the central processing unit 112 of FIG. 1 and stored in the memory 114 of FIG. 1. It is to be understood that the positions 604 are not practically preformed in the human mind as this calculation is done on a stream of the note tokens 508 read from the memory 114.

Referring now to FIG. 7, therein is shown a table of a keyword map 702 for the required keyword decision step 210 of FIG. 2. The keyword map 702 can include keywords 704. The keywords 704 can include the required keywords 306 of FIG. 3, the secondary keyword 414 of FIG. 4, and the primary keyword 418 of FIG. 4.

That is, the keywords 704 can summed to provide a total number of keywords associated with the classification code 106 of FIG. 1, which could be zero or more. In practice, it is contemplated that the keywords 704 could be the morphology keywords from the ICD-O-3 morphology classification code, for example. The keyword map 702 can include a keyword position 706.

The keyword position 706 can be the position 604 associated with the keywords 704 based on the keywords 704 matching the note tokens 508 of FIG. 5. As shown, the required keywords 306, the secondary keywords 414, and the primary keywords 418 can be matched to the note tokens 508, and the positions 604 of the note tokens 508 will be associated with their respective keywords 704 as the keyword positions 706. In alternative embodiments, it is contemplated that the keyword position 706 can be the position of the keyword 704 within the note 102 of FIG. 1.

A unique keyword map 702 can be created for each row in the classification code table 302 of FIG. 3. That is, for each of the classification codes 106, which corresponds to each morphology code in the ICD-O-3 morphology classification code, a unique keyword map 702 can be created.

The keyword map 702 can be constructed by first determining which of the note tokens 508 are also the keywords 704. For illustrative purposes, the keyword map 702 depicts the third classification code 106 within the classification code table 302 of "503/1" having the keywords 704: "chuck", "much", "wood", and "toothpaste". The keywords 704 for this classification code 106 are listed in the left column.

As will be appreciated, "chuck", "much", and "toothpaste" are not listed as the required keyword 306 within the classification code table 302. However, "chuck", "much", and "toothpaste" may be secondary keywords 414 or primary keywords 418.

The classification code parser 100 can determine which of the keywords 704 are present within the note token position table 602. When one of the keywords 704 matches with one of the note tokens 508, the keyword 704 should be considered a matched keyword and the token position 604 of FIG. 6 is recorded as the keyword position 706 for the matched keyword within the keyword map 702.

A total number of the matched keywords can be calculated by adding up the number of the keywords 704 within the keyword map 702 having an associated position 604, which could be zero or more. Illustratively, for example, the keyword 704 "toothpaste" is not in the note tokens 508 and should therefore not be considered a matched keyword, while the other keywords 704 "chuck", "much", and "wood" are matched keywords.

If the keyword 704 is found more than one time within the note token position table 602, then multiple token positions 604 can be recorded for the keyword position 706. The note token "chuck", for example, is depicted in FIG. 6 as having positions 6 and 11. As such, position 6 and 11 are recorded as the keyword position 706 for "chuck".

Referring now to FIG. 8, therein is shown a table of a required keyword test 802 for the required keyword decision step 210 of FIG. 2. The required keyword test 802 can evaluate both the keywords 704 and the keyword positions 706.

That is, once the keyword map 702 of FIG. 7 between the note tokens 508 of FIG. 5 and the keywords 704 has been constructed, it must pass two tests in order for the match between the note 102 of FIG. 1 and the classification code 106 of FIG. 1 to be considered further. These tests are the required keyword decision step 210 and primary keyword decision step 212 of FIG. 2.

Particularly regarding the required keyword decision step 210, this test determines the presence of all of the required keywords 306 for the classification code 106 of FIG. 1. As shown, the required keyword 306 is "wood", which is present as one of the note tokens 508 with the keyword position 706 of 2 and 12.

The note 102 therefore passes the required keyword decision step 210. However, for example, if the required keyword 306 included "toothpaste", which is not present as a note token 508 within the note 102, the note 102 would then be rejected at the required keyword decision step 210.

Figures 9, 10:
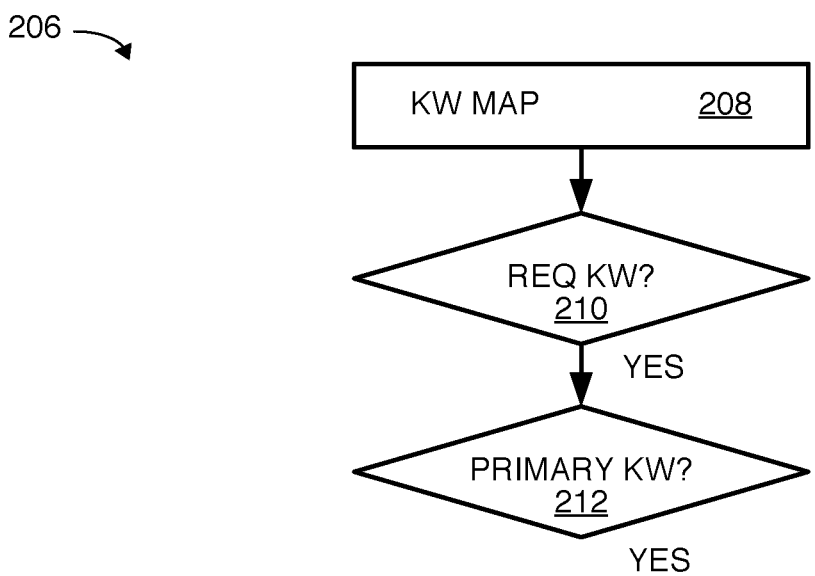
FIG. 9 is a table of a primary keyword test for the primary keyword decision step of FIG. 2.
FIG. 10 is a control flow of the matching step of FIG. 2.

Referring now to FIG. 9, therein is shown a table of a primary keyword test 902 for the primary keyword decision step 212 of FIG. 2. The primary keyword test 902 can evaluate both the keywords 704 and the keyword positions 706.

That is, once the keyword map 702 of FIG. 7 between the note tokens 508 of FIG. 5 and the keywords 704 has been constructed, it must pass the primary keyword decision step 212. The primary keyword decision step 212 determines the presence of at least one of the primary keywords 418 of FIG. 4 within the note tokens 508.

The primary keywords 418 are any of the description tokens, from the descriptions 304 of FIG. 3 for any specific classification code 106 of FIG. 1, that are not secondary keywords 414 of FIG. 4 or ignored tokens 416 of FIG. 4. As shown, the primary keyword 418 is "chuck". Since the primary keyword decision step 212 only requires a single primary keyword 418 to be present within the note tokens 508, the note 102 passes the primary keyword decision step 212.

Referring now to FIG. 10, therein is shown a control flow of the matching step 206 of FIG. 2. The matching step 206 can begin with the keyword mapping step 208 where the note token position table 602 of FIG. 6 and the keyword map 702 of FIG. 7 is created.

That is, the token position 604 of FIG. 6 for each of the note tokens 508 of FIG. 5 are listed together within the note token position table 602. The note token position table 602 is used to create the keyword map 702 by extracting the token position 604 of each keyword 704 of FIG. 7.

Once the keyword map 702 is created, the note tokens 508 must pass two tests in order for the match between the note 102 of FIG. 1 and the classification code 106 of FIG. 1 to be considered further. The first test is the required keyword decision step 210 which determines the presence of all of the required keywords 306 of FIG. 3 within note tokens 508.

The required keyword test 802 of FIG. 8 depicts the required keyword decision step 210 running with the required keywords 306 and the keyword positions 706. The keyword 704 "wood" is shown as the required keyword 306, and since the note tokens 508 include the required keyword 306 at positions 2 and 12, the note 102 passes the required keyword decision step 210.

The second test is the primary keyword decision step 212 which determines the presence of at least one of the primary keywords 418 within the note tokens 508. The keyword 704 "chuck" is shown as the primary keyword 418, and since the note tokens 508 include at least one of the primary keywords 418, "chuck" at positions 6 and 11, the note 102 passes the primary keyword decision step 212.

Figure 11:
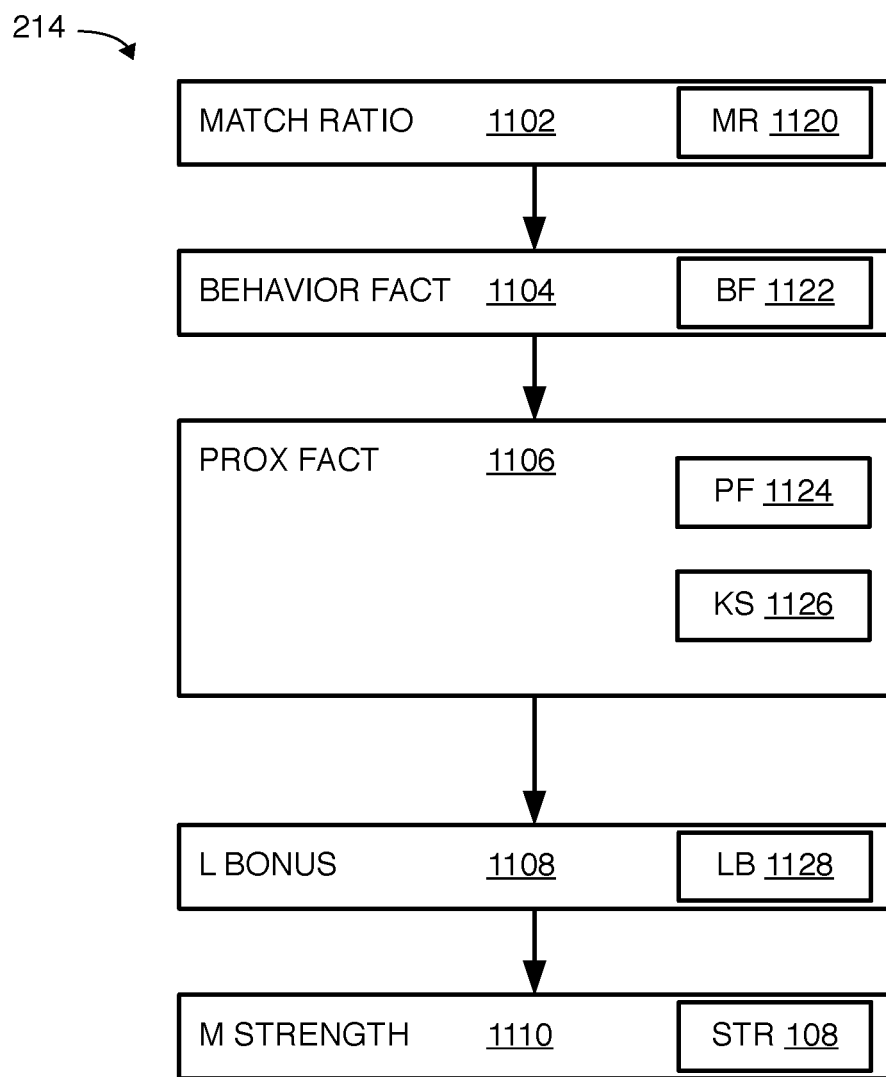
FIG. 11 is a control flow of the calculate step of FIG. 2.

Referring now to FIG. 11, therein is shown a control flow of the calculate step 214 of FIG. 2. The calculate step 214 can provide a result as the strength 108 between the note 102 of FIG. 1 and one of the classification codes 106 of FIG. 1. The strength 108 for each of the notes 102 can be calculated based on hundreds or even thousands of possible classification codes 106; as such it is contemplated that the calculate step 214 is implemented utilizing the central processing unit 112 of FIG. 1 which can automatically determine the strength 108 of a match for many notes in a very short amount of time.

As such the calculate step 214, does not use manual classification techniques, but instead controls the technical functioning of the central processing unit 112 and thereby solves the technical problems described above that are found in NLPs, and the central processing unit 112 is to be considered an essential element in this solution. Furthermore, it is to be understood that the calculate step 214 utilizes technical functions such as note token streams that must be manipulated by a central processing unit to be useful and to solve the technical problems set forth herein.

The strength 108 of a match between the note 102 and the classification code 106 can be calculated within the central processing unit 112 by executing a calculate match ratio step 1102, a calculate behavior factor step 1104, a calculate proximity factor step 1106, a calculate length bonus step 1108, and a calculate final match strength step 1110.

The result of the calculate step 214 is a single floating point value representing the strength 108 of the match. A higher score corresponds to a stronger match.

The calculate match ratio step 1102 can determine a match ratio 1120 based on a relative number of keywords 704 of FIG. 7 that are present in the note tokens 508 of FIG. 5. The higher the match ratio 1120, the stronger the match between the note 102 and the classification code 106. This relationship is reflected in the match ratio 1120, which is calculated as follows:

$$\text{Match Ratio} = k^2/m \qquad \text{Equation 1}$$

where k=the total number of the matched keywords in the keyword map 702 of FIG. 7, and where m=the total number of the keywords 704 assigned to the classification code 106. Illustratively, for example, if the classification code 106 has a total number of 4 keywords and the note 102 includes a total number of 3 matched keywords, then the match ratio 1120 is:

$$\text{Match Ratio} = 3^2/4 = 9/4 = 2.25. \qquad \text{Equation 2}$$

Once the match ratio 1120 is calculated, the classification code parser 100 of FIG. 1 can execute the calculate behavior factor step 1104. Because the classification code parser 100 can be implemented with the ICD-O-3 morphology codes used for cancer pathology notes, the calculate behavior factor step 1104 can emphasizes malignant behavior unless the morphology of the classification code 106 is definitely non-invasive.

This emphasis is captured in a behavior factor 1122. The behavior factor 1122 is calculated based on the behavior code 310 of FIG. 3 and the description 304 of FIG. 3 for the classification code 106 matching the note 102, which is calculated as follows:

If the behavior code is "3"; or if the behavior code is "2" and the description contains the keyword "non-invasive";

then the behavior factor is 1.5 otherwise, the behavior factor is 1.0. Equation 3

Once the calculate behavior factor step 1104 has been completed to provide the behavior factor 1122, the classification code parser 100 can execute the calculate proximity factor step 1106. A tight cluster of matching keywords 704 within the note 102 indicates a match between the note 102 and the classification code 106 will have a higher strength 108 than if the same keywords 704 were scattered throughout the note 102. This relationship between the keywords 704 within the note 102 is captured in a proximity factor 1124.

The first step in calculating the proximity factor 1124 can include calculating a keyword span 1126. The keyword span 1126 can be the length of the shortest span within the note token stream that contains all the matched keywords in the keyword map 702. That is, the keyword span 1126 can be the shortest span of the positions 604 of FIG. 6 within the note token position table 602 of FIG. 6 to contain at least one instance of each of the keywords 704, which is calculated as follows:

$$\text{Highest Position} - \text{Lowest Position} + 1 = \text{Keyword Span} \qquad \text{Equation 4}$$

Utilizing the keyword map 702, the classification code 106 has the keywords 704 "chuck", "much", and "wood". The note token position table 602 shows the position 604 of "much" to be 1, while the position 604 of "chuck" is 6 and 11, and the position 604 of "wood" is 2 and 12.

In this case, the span between 1 and 6 contains at least one instance of all the keywords 704. 6 would be considered the highest position 604, while 1 would be considered the lowest position 604 giving the keyword span 1126 of:

$$\text{Keyword Span} = 6 - 1 + 1 = 6 \qquad \text{Equation 5}$$

In an alternative example, if the classification code 106 had the keywords 704 "chuck" at positions 6 and 11 and "wood" at positions 2 and 12, but did not include the keyword 704 "much", the calculation would differ. Illustratively, in this alternative case the shortest span containing all of the keywords 704 would be between the positions 604 11 and 12, giving the keyword span 1126 of:

$$\text{Keyword Span} = 12 - 11 + 1 = 2 \qquad \text{Equation 6}$$

Once the keyword span 1126 has been calculated, the proximity factor 1124 is determined as follows:

$$\text{Proximity Factor} = 1/(1 + e/50) \qquad \text{Equation 7}$$

where e ("excess")=the larger of (s−m) and 0; where s=keyword span 1126; and where m=the number of keywords 704 in the classification code 106.

The proximity factor 1124, for the note 102 having the note token position table 602 of FIG. 6 and the keyword map 702 of FIG. 7, can be calculated using the keyword span 1126 of 6 as follows:

$$\text{Proximity Factor} = 1/(1 + (6-3)/50) = 0.943 \qquad \text{Equation 8}$$

Note that the larger the excess, the looser the cluster, and the lower the proximity factor 1124. In some cases, two different classification code 106 morphologies are both good matches to the note 102, but one might be more specific than the other.

For example, "sarcoma" and "liposarcoma" might both appear in the note 102, but since "liposarcoma" is specific, we want the classification code parser 100 to choose it. This is accomplished by giving a length bonus 1128 for longer keywords 704 in a match. This bonus is calculated in the calculate length bonus step 1108 as follows:

$$\text{Length Bonus} = 0.01 * \Sigma b_k \qquad \text{Equation 9}$$

where $b_k$=the larger of (c−6) and 0; where c=number of characters in the keyword 704; and where Σ indicates that the $b_k$ for each of the keywords 704 should be summed.

Calculating the length bonus 1128 for the keyword map 702 of FIG. 7, would yield the length bonus 1128 of 0 because $b_k$ for each of the keywords 704 would be 0 as none of the keywords 704 are larger than 6 characters. In an alternative example where the keyword map included the keywords "liposarcoma" with 11 characters and "sarcoma" with 7 characters, the length bonus 1128 would be calculated as:

$$\text{Length Bonus}=0.01*\Sigma(9,1)=0.06 \qquad \text{Equation 10}$$

The length bonus 1128 can be added to the strength 108 of the entire match. The strength 108 of the match between the note 102 and the classification code 106 can be calculated with the calculate final match strength step 1110 by first multiplying the match ratio 1120 with the behavior factor 1122 and the proximity factor 1124, as such:

$$x=m*b*p \qquad \text{Equation 11}$$

where "m" is the match ratio 1120, "b" is the behavior factor 1122, and "p" is the proximity factor 1124. Next the final value of the strength 108 can be:

$$\text{If } x>0 \text{ then strength}=x+lb;$$

$$\text{Else strength}=x \qquad \text{Equation 12}$$

where "lb" is the length bonus 1128.

As described, the classification code parser 100 utilizes methods not used by human note takers if they decide to include a classification code 106 with the note 102. Rather, these steps describe technical means for controlling the central processing unit 112, memory 114, and input/output elements 116, and to automatically associate the classification code 106 with the notes 102, a particular technical improvement over prior systems.

Moreover, the classification code parser 100 solves a problem with prior technologies, specifically with NLPs and with statistical or machine learning NLPs. These prior methods suffer from the inability to robustly parse text where formal grammar and vocabulary are not used.

The classification code parser 100 addresses this inability by digitizing, tokenizing, and matching keywords which overcomes the prior solutions' reliance on guess and check training with large data sets, and the prior solutions' reliance on formal vocabulary and grammar.

Furthermore, it is to be understood that the steps herein are not practically performed in the human mind. In particular, the steps of digitizing the text 104 of the note 102 and tokenizing the digital text, together with the other disclosed steps, control the technical process or the internal functioning of the computer itself or its interfaces and practically prevents the classification code parser 100 from being performed in the mind.

Thus, it has been discovered that the classification code parser 100 furnishes important and heretofore unknown and unavailable technical solutions and capabilities in automated parsing and classification code assignment. The match ratio 1120, the behavior factor 1122, the proximity factor 1124, the length bonus 1128, and the strength 108 are all intended to be calculated using the central processing unit 112, and it is these calculations both individually and in combination that enable the notes 102 to be matched with the classification code 106, something that prior technologies are unable to provide. The resulting configurations are straightforward, cost-effective, uncomplicated, highly versatile, accurate, sensitive, and effective, and can be implemented by adapting known components for ready, efficient, and economical manufacturing, application, and utilization.

While the classification code parser 100 has been described in conjunction with a specific best mode, it is to be understood that many alternatives, modifications, and variations will be apparent to those skilled in the art in light of the preceding description. Accordingly, it is intended to embrace all such alternatives, modifications, and variations, which fall within the scope of the included claims. All matters set forth herein or shown in the accompanying drawings are to be interpreted in an illustrative and non-limiting sense.

What is claimed is:

1. A method comprising:
   obtaining a classification code and a text;
   generating, from the text, a note token stream, wherein the note token stream includes a note token and a position of the note token, wherein generating the note token stream comprises: removing negative content identified from the text, the negative content comprising a portion of the text starting with a negative term;
   generating a keyword map including a keyword associated with the position based on the keyword matching the note token, and the keyword map including a total number of matched keywords associated with the classification code;
   determining a match ratio from the total number of the matched keywords and the total number of the keywords;
   determining a proximity factor based on a keyword span; and
   determining a strength of a match between the classification code and the text based on the match ratio and the proximity factor.

2. The method of claim 1, wherein the classification code includes an ICD-O-3 code and a behavior code.

3. The method of claim 2, comprising determining a behavior factor according to the following equation:
   if the behavior code is "3" or if the behavior code is "2" and the text includes "non-invasive", then the behavior factor is 1.5;
   otherwise, the behavior factor is 1.0; and wherein determining the strength includes multiplying the match ratio, the proximity factor, and the behavior factor.

4. The method of claim 1, wherein determining the match ratio includes determining the match ratio according to the following equation:
   match ratio=$k^2$/m, where k is the total number of the matched keywords and where m is the total number of the keywords.

5. The method of claim 1, wherein determining the proximity factor includes determining the proximity factor according to the following equation:
   proximity factor=1/(1+e/50), where e is a largest value between (s−m) and 0, where s is the shortest span of tokens within the note token stream including the matched keywords, and where m is a total number of the keywords in the classification code.

6. The method of claim 1, wherein generating the keyword map comprises:
   reading a secondary keyword and an ignored token;
   determining a primary keyword as any of the keywords that are not a required keyword, the secondary keyword, or the ignored token; and
   determining whether the primary keyword matches a second note token within the note token stream.

7. The method of claim 1, wherein generating the note token stream further includes:
 reading a special token; and
 converting the text to lowercase unless the text matches the special token.

8. The method of claim 1, wherein generating the note token stream further includes:
 obtaining a descriptive synonym; and
 replacing the note token with the descriptive synonym based on the note token matching the descriptive synonym.

9. The method of claim 1, wherein generating the note token stream further includes:
 splitting the text into a plurality of sentences;
 identifying a negative term from one of the plurality sentences; and
 deleting a portion of the sentence of the plurality of the sentences from the negative term to an end of the sentence.

10. The method of claim 1, wherein the keyword span is the shortest span of tokens within the note token stream including the matched keywords.

11. The method of claim 1, wherein determining the strength includes multiplying the match ratio and the proximity factor.

12. The method of claim 1, comprising tokenizing the text of the note to create the note token stream.

13. A non-transitory computer readable medium storing instructions that, when executed, cause one or more processors to:
 obtain a classification code and a text;
 generate, from the text, a note token stream, wherein the note token stream includes a note token and a position of the note token, wherein generating the note token stream comprises:
 removing negative content identified from the text, the negative content comprising a portion of the text starting with a negative term;
 generate a keyword map including a keyword associated with the position based on the keyword matching the note token, and the keyword map including a total number of matched keywords associated with the classification code;
 determine a match ratio from the total number of the matched keywords and the total number of the keywords;
 determine a proximity factor based on a keyword span; and
 determine a strength of a match between the classification code and the text based on the match ratio and the proximity factor.

14. The computer readable medium of claim 13, wherein the classification code includes an ICD-O-3 code and a behavior code.

15. The computer readable medium of claim 13, comprising instructions causing the one or more processors to determine a behavior factor according to the following equation:
 if the behavior code is "3" or if the behavior code is "2" and the text includes "non-invasive", then the behavior factor is 1.5;
 otherwise, the behavior factor is 1.0; and
 wherein the instructions cause the one or more processors to multiply the match ratio, the proximity factor, and the behavior factor.

16. The computer readable medium of claim 13, wherein determining the match ratio comprises determining the match ratio according to the following equation:
 match ratio=$k^2$/m, where k is the total number of the matched keywords and where m is the total number of the keywords.

17. The computer readable medium of claim 13, wherein determining the proximity factor comprises determining the proximity factor according to the following equation:
 proximity factor=1/(1+e/50), where e is a largest value between (s-m) and 0, where s is the shortest span of tokens within the note token stream containing all the matched keywords, and where m is a total number of the keywords in the classification code.

18. The computer readable medium of claim 13, wherein generating the keyword map comprises:
 read a secondary keyword and an ignored token;
 determine a primary keyword as any of the keywords that are not a required keyword, the secondary keyword, or the ignored token; and
 determine whether the primary keyword matches a second note token within the note token stream.

19. The computer readable medium of claim 13, wherein generating the note token stream comprises:
 reading a special token; and
 converting the text to lowercase unless the text matches the special token.

20. The compute readable medium of claim 13, wherein generating the note token stream comprises:
 obtaining a descriptive synonym; and
 replacing the note token with the descriptive synonym based on the note token matching the descriptive synonym.

21. The computer readable medium of claim 13, wherein generating the note token stream comprises:
 splitting the text into a plurality of sentences;
 identifying a negative term from one of the plurality sentences; and
 deleting a portion of the sentence of the plurality of the sentences from the negative term to an end of the sentence.

22. The computer readable medium of claim 13, wherein the keyword span is the shortest span of tokens within the note token stream including the matched keywords.

23. The computer readable medium of claim 13, wherein determining the strength includes multiplying the match ratio and the proximity factor.

24. The computer readable medium of claim 13, wherein the instructions comprise instructions causing the one or more processors to tokenize the text of the note to create the note token stream.

* * * * *

UNITED STATES PATENT AND TRADEMARK OFFICE
CERTIFICATE OF CORRECTION

PATENT NO. : 11,886,819 B2  
APPLICATION NO. : 18/166158  
DATED : January 30, 2024  
INVENTOR(S) : Brian Berns and Kirk Junker Page 1 of 1

It is certified that error appears in the above-identified patent and that said Letters Patent is hereby corrected as shown below:

In the Claims

In Column 18 Line 34 In Claim 20, delete "compute" and insert --computer--.

Signed and Sealed this
Twenty-sixth Day of November, 2024

Katherine Kelly Vidal
*Director of the United States Patent and Trademark Office*